US006420064B1

(12) United States Patent
Ghosh et al.

(10) Patent No.: US 6,420,064 B1
(45) Date of Patent: Jul. 16, 2002

(54) COMPOSITE ELECTRODES FOR SOLID STATE DEVICES

(75) Inventors: Debabrata Ghosh; Frank Martel; Zheng Tang, all of Calgary (CA)

(73) Assignee: Global Thermoelectric Inc., Calgary (CA)

( * ) Notice: Subject to any disclaimer, the term of this patent is extended or adjusted under 35 U.S.C. 154(b) by 0 days.

(21) Appl. No.: 09/684,660

(22) Filed: Oct. 10, 2000

Related U.S. Application Data (60) Provisional application No. 60/158,124, filed on Oct. 8, 1999, and provisional application No. 60/231,542, filed on Sep. 11, 2000.

(51) Int. Cl.[7] .............................................. H01M 4/86
(52) U.S. Cl. ............................ 429/40; 429/30; 429/33; 429/41; 429/42; 204/282; 204/283
(58) Field of Search ............................ 429/33, 40, 41, 429/42, 30; 204/282, 283

(56) References Cited

U.S. PATENT DOCUMENTS

| 3,219,730 A | 11/1965 | Bliton et al. |
| 3,300,344 A | 1/1967 | Bray et al. |
| 3,551,209 A | 12/1970 | Alles et al. |
| 3,787,244 A | 1/1974 | Schulmesiter et al. |
| 4,459,341 A | 7/1984 | Marachant et al. |
| 4,582,766 A | 4/1986 | Isenberg et al. |
| 4,597,170 A | 7/1986 | Isenberg |
| 4,702,971 A | 10/1987 | Isenberg |
| 4,767,518 A | 8/1988 | Maskalick |
| 4,839,327 A | 6/1989 | Haruta et al. |

(List continued on next page.)

FOREIGN PATENT DOCUMENTS

| EP | 0 351 123 | 1/1990 |
| EP | 0 424 813 A1 | 10/1990 |
| EP | 0 526 749 A1 | 2/1993 |
| EP | 0 584 551 A1 | 3/1994 |
| EP | 0 996 184 A2 | 4/2000 |

(List continued on next page.)

OTHER PUBLICATIONS

Gauckler, Professor Ludwig, J.;; Experimental papers carried out by the Department of Materials, Swiss Federal Institute of Tech., Zurich, Mar. 1966 to Dec. 1999.

Virkar, Anil V.; Various articles presented by Dr. Virkar—Professor of Materials Science & Eng. University of Utah, No month/year/available.

Swartz, et al.; Paper—"Cathode Supported Thin–Film Solid Oxide Cells with Low Operating Temperatures", NexTech Materials Ltd., Worthington, OH., No month/year available.

Anderson, et al.; Project Fact Sheet "Low Temperature Cathode Supported Electrolytes"—United States Department of Energy—2000/2001, No month available.

Argirusis, et al.; Paper Preparation and Characterization of Cathode Supported SOFC's with MOD Thin–Film Electrolytes.

(List continued on next page.)

Primary Examiner—Bruce F. Bell
(74) Attorney, Agent, or Firm—Bennett Jones LLP (57) ABSTRACT

A solid state ionic device includes a dense electrolyte sandwiched between two porous electrodes. In one embodiment, the device is anode supported and the cathode is formed of a porous three-dimensional solid phase structure having an electrocatalytic phase of a plurality of electrocatalytic particles and an ionic conducting phase of a plurality of ionic conductor particles. The mean or median size of the electrocatalytic particles is larger than the mean or median size of the ionic conductor particles. The device may further include a long range electronic conducting layer of lantham cobaltate or other electronically conducting material.

29 Claims, 9 Drawing Sheets

U.S. PATENT DOCUMENTS

| | | | |
|---|---|---|---|
| 4,849,254 | A | 7/1989 | Spengler et al. |
| 4,933,054 | A | 6/1990 | Mazanec et al. |
| 4,940,528 | A | 7/1990 | Oki et al. |
| 5,037,525 | A | 8/1991 | Badwal |
| 5,045,169 | A | 9/1991 | Feduska et al. |
| 5,208,207 | A | 5/1993 | Stonehart et al. |
| 5,286,580 | A | 2/1994 | Ippommatsu et al. |
| 5,294,580 | A | 3/1994 | Dufner |
| 5,306,411 | A | 4/1994 | Mazanec et al. |
| 5,500,307 | A | 3/1996 | Anzai et al. |
| 5,543,239 | A | 8/1996 | Virkar et al. |
| 5,591,315 | A | 1/1997 | Mazanec et al. |
| 5,670,270 | A | 9/1997 | Wallin |
| 5,676,806 | A | 10/1997 | Berkel et al. |
| 5,693,212 | A | 12/1997 | Mazanec et al. |
| 5,744,015 | A | 4/1998 | Mazanec et al. |
| 5,753,385 | A | 5/1998 | Jankowski et al. |
| 5,824,429 | A | 10/1998 | Das et al. |
| 5,863,673 | A | 1/1999 | Campbell et al. |
| 5,937,264 | A | 8/1999 | Wallin |
| 5,993,986 | A | 11/1999 | Wallin et al. |
| 5,993,988 | A | 11/1999 | Ohara et al. |
| 5,998,056 | A | 12/1999 | Divisek et al. |
| 6,051,329 | A | 4/2000 | Fasano et al. |
| 6,054,232 | A | 4/2000 | Ippommatsu et al. |
| 6,117,582 | A | 9/2000 | Wallin et al. |

FOREIGN PATENT DOCUMENTS

| | | |
|---|---|---|
| EP | 1 058 329 A2 | 12/2000 |
| FR | 1.513.898 | 3/1967 |
| GB | 2 305 169 A | 4/1997 |
| GR | 1.189221 | 3/1966 |
| JP | 6327-1807 | 11/1988 |
| JP | 02-310459 | 12/1990 |
| JP | 04-051462 | 2/1992 |
| JP | 04-192261 | 7/1992 |
| JP | 174833 | 7/1993 |
| JP | 7045293 | 2/1995 |
| JP | 10-021930 | 1/1998 |
| JP | 10-021931 | 1/1998 |
| WO | PCT/BG98/00016 | 4/1999 |
| WO | PCT/US99/03865 | 8/1999 |
| WO | PCT/NL99/00269 | 11/1999 |
| WO | PCT/US99/13132 | 12/1999 |
| WO | PCT/DK99/00631 | 5/2000 |
| WO | PCT/US00/05735 | 9/2000 |

OTHER PUBLICATIONS

Paper B–IN–05 12th International Conference on Solid State Ionics—Halkidiki, 1999 High Performance Electrodes for Medium–Temperature—Solid Oxide Fuel Cells—Hiroyuki Ochida, et al.—Yamanashi University, Takeda 4–3, Kofu 400–8511, Japan, No month available.

Journal of Power Sources 61 (1996) 205–211—Catalysis of the electrochemical processes of solid oxide fuel cell cathodes—J.W. Erning et al, No month available.

J. Electrochem. Soc., vol. 141. No. 8. Aug. 1994—Electroless Deposition of Electroddes in Solid–Oxide Fuel Cells—M.M. Murphy, et al.

Solid State Ionics 113–115 (1998) Pd–promoted La0.6Sr0.4CO0.2FE0.8o3 Cathodes—M. Sahibzada, et al., Department of Materials, Imperial College of Science, London, No month available.

Paper—Electrode Reaction at Fixed Platinum Film—Fixation of Platinium Film on Stabilized–Zirconia Electrolvte and Its Effect on the Electrode Performance of the Solid–Electrolvte Fuel Cell—Nakagawa. et, No month/year available.

Paper B–KE–04—12th International Conference on Solid State Ionics—Halkidiki, 1999—Characterisation and Performance of SofC Electrodes: A Critical Analysis—Mogensen, et al, No month available.

12th International Conference on Solid State Ionics—Halkidiki, 1999—Paper B–IN–05 Uchida, et al, High Performance Electrodes for Medium–Temperature Solid Oxide Fuel Cells, etc, No month available.

Journal of Power Sources 61 (1996) 205–211. "Catalysis of the electrochemical processes on solid oxide fuel cell cathodes"—Paper by J.W. Erning, et al. Institute of Energy Process Engineering, No month available.

Electrochemical Society vol. 141. No. 8. Aug. 1994 "Electroless Deposition of Electrodes in Solid–Oxide Fuel Cells" Paper by M.M. Murphy, et al.

Department of Materials, Imperial Collect of Science "Pd–promoted La0.6Sr0.4Co0.2Fe0.803 cathodes" Paper by M. Sahibzada, et al.—Solid State Ionics, No month/year available.

Journal of Chemical Engineering of Japan, vol. 25 No. 1, 1992—Electrode Reaction at Fixed Platinum Film—Fixation of Platinum Film, etc.—Paper by Nakagawa, et al, No month available.

12th International Conference on Solid State Ionics—Halkidiki 1999—Characterization and Performance of SofC Electrodes: A Critical Analysis –Paper by Mogensen, et al, No month available.

COMPOSITE ELECTRODES FOR SOLID STATE DEVICES

CROSS-REFERENCE TO RELATED APPLICATIONS

This application claims the priority benefit of U.S. Provisional Application No. 60/158,124 filed on Oct. 8, 1999 (Solid Oxide Fuel Cell Composite Electrode), and No. 60/231,542, filed Sep. 9, 2000 (Improved Composite Electrodes For Solid State Devices), which applications are incorporated herein by reference in their entirety.

FIELD OF THE INVENTION

The present invention relates to composite electrodes and functional layers for electrode reactions for use with solid-state ionic devices, and solid oxide fuel cells in particular.

BACKGROUND OF THE INVENTION

The following references are referred to herein by their numerical reference and the contents of each is incorporated herein by reference.
1. Erning, J. W., Hauber, T., Stimming, U. Wippermann, K., Catalysis of the electrochemical processes on solid oxide fuel cell cathodes, Journal of Power Sources 61 (1996) 205–211.
2. M. Watanabe, H. Uchida, M. Shibata, N. Mochizuki and K. Amikura, High performance catalyzed-reaction layer for medium temperature operating solid oxide fuel cells, J. Electrochem. Soc., vol. 141, (1994) 342–346.
3. Sahibzada, M., Benson, S. J., Rudkin, R. A., Kilner, J. A., Pd-promoted $La_{0.6}Sr_{0.4}Co_{0.2}Fe_{0.8}O_3$ cathodes. Solid State Ionics 113–115 (1998) 285–290.
4. M. M. Murphy, J. Van herle, A. J. McEvoy, K. Ravindranathan Thampi, Electroless deposition of electrodes in solid oxide fuel cells, J. Electrochem. Soc., vol. 141 (1994) 30 L94–96.
5. Uchida et al. Shin-ichi Arisaka and Masahiro Watanabe, Paper B-IN-05 at $121^{st}$ International Conference on Solid State Ionics (1999) 154–155.

Background

Solid state ionic devices typically consist of a fully dense electrolyte sandwiched between thin electrode layers. It is known that the principal losses in most solid state ionic devices occur in the electrodes or the electrode/electrolyte interfaces. Therefore, minimization of these losses is critical to efficient operation of these devices.

Solid oxide fuel cells (SOFC) are theoretically very efficient energy conversion devices that have the potential of becoming a commercial product for numerous uses. A SOFC is a solid electrochemical cell which consists of a solid electrolyte impervious to gases, sandwiched between a porous cathode and a porous anode. Oxygen gas is transported through the cathode to its interface with the electrolyte where it is reduced to oxygen ions, which migrate through the electrolyte to the anode. At the anode, the ionic oxygen reacts with fuels such as hydrogen or methane and release electrons. The electrons travel back to the cathode through an external circuit to generate electric power.

The construction of conventional SOFC electrodes are well known. Electrodes are often applied as composites of an electron conducting material and an ion conducting material. For instance, an anode may consist of electronic conducting nickel (Ni) and ionic conducting yttria stabilized zirconia (YSZ) while the cathode may consist of a perovskite such as $La_{1-x}Sr_xMnO_{3-\delta}$ (LSM) as the electron conducting material and YSZ as the ion conductor.

Conventional SOFCs exhibit high performance at operating temperatures of 1000° C. However, such high temperature operation has disadvantages such as physical or chemical degradation of the construction materials. Therefore, it is desirable to reduce the operating temperature of a SOFC stack to a medium temperature of about 700° C. However, at such medium temperatures, electrode reaction rates decrease significantly. Prior art efforts to increase electrode reactivity at lower temperatures have focussed on optimizing the electrode microstructure and by introducing catalytic materials into the electrode structure.

It is well known to provide an activated surface on the fuel cell electrodes by means of a catalyst to aid the electrochemical process. Nickel is commonly used as a catalyst on the anode side for oxidation of fuel. On the cathode side, ceramic cathode materials typically used in SOFCs, such as perovskites have a high activation energy for oxygen reduction. Therefore, the activation energy may be reduced for the oxygen reduction reaction by adding noble metals such as Au, Ag, Pt, Pd, Ir, Ru and other metals or alloys of the Pt group. Erning et al. [1] reported that addition of highly dispersed noble metals ($<=0.1$ mg/cm$^2$) lowers the activation energy of the oxygen reduction reaction at the cathode of an SOFC. M. Watanabe [2] also found that the anodic polarization resistance and its activation energy were greatly decreased by loading only a small amount of catalyst such as Ru, Rh, and Pt onto a samaria-doped ceria (SDC) anode. A large depolarizing effect was also observed with a Pt-catalyzed LSM cathode, especially at high current densities. Sahibzada et al. [3] has recently reported that LSCF electrodes which were impregnated with small amounts of Pd resulted in 3–4 times lower cathodic impedance in the temperature range 400 to 750° C. The overall cell resistance decreased 15% at 6500 C. and 40% at 550° C.

For economic reasons, noble metal catalysts are applied in very small amounts to catalyze the electrochemical process at electrodes. The catalysts are conventionally impregnated in the pores of the electrode by a filtration or a chemical process. The impregnation process is frequently followed by a binding process where a binder is superimposed on the deposited particles to provide a secure and durable attachment of the coating with the base material. U.S. Pat. Nos. 3,097,115; 3,097,974; 3,171,757 and 3,309,231 disclose such conventional impregnating processes for porous electrodes.

The catalysts may also be applied by common electroless deposition techniques for Ni, Pd and Ag [4] and replacement plating, as disclosed in U.S. Pat. No. 3,787,244. In this process, an acidic plating solution containing a salt of a noble metal catalyst is forced through the pores of a nickel electrode substrate and the noble metal ions from the dissolved salt replace a thin layer of the nickel surface within the pores.

It is known [1] to form highly dispersed catalyst layers with an amount of less than 0.1 mg/cm$^2$ from aqueous solutions of Pt, Pd, Ir or Ru salts. A few drops of these solutions were applied onto the electrolyte surface. After drying, the salts were either reduced to metal form by heating under hydrogen (Pt and Pd) or oxidized by heating under air (Ir and Ru), Most recently, Uchida et al. [5] applied nanometer-sized noble metal catalysts to both anode and cathode resulting in appreciably lower overpotential ohmic resistance.

Singheiser (EP 424813) discloses an intermetallic compound layer (0.5–5 µm) contains 2–70 wt. % of a noble metal such as Pt, Ag or Pd which can be used between electrolyte and electrodes, or to connect electrically two fuel-cells. It is claimed that the fuel cell can be operated at a lower temperature due to higher electrode conductivity.

Because of the cost of noble metals, the application of noble metals in SOFC electrodes so far are mainly limited to its catalytic abilities. All recent efforts have been to add very fine particles of the catalyst in order to maximize the three phase boundary of the catalyst, the gas phase and the electrolyte. The catalyst is either applied as a very thin layer at the electrolyte/electrode boundary or is widely dispersed throughout the electrode.

In U.S. Pat. No. 5,543,239 issued to Virkar et al., an electrocatalyst is incorporated into a electrode microstructure that is claimed to improve the performance of a solid state ionic device by providing a catalyst and by improving electrical conductance. In this disclosure, a porous ionic conductor is applied to a dense electrolyte substrate. An electrocatalyst is then introduced into the porous matrix to produce electrical continuity and a large three phase boundary line length. As a result, the electrocatalyst is applied as a thin layer of small particles over the ionic conductor.

The electrode disclosed by Virkar et al., however, does not solve the problem of electrode instability. It is known that vapor loss of noble metals occurs at even medium SOFC operating temperatures. According to the Thomson-Freundlich (Kelvin) equation, an important aspect of the vapor pressure difference across a curved surface is the increase in vapor pressure at a point of high surface curvature. Thus, the smaller the particle size, the higher the vapor pressure. This could cause significant vapor loss for small noble metal particles at SOFC operating temperatures.

Furthermore, higher vapor pressure at the particle surface and lower vapor pressure at a neck between two particles makes smaller particles much easier to be sintered. Thus, the microstructure of an electrode with submicronic noble metal (<0.5 µm) particles is not stable at medium to high SOFC operating temperatures, and especially when the electrode handles high current.

Furthermore, a thin electronic conducting layer at the electrode will have large ohmic resistance at the electrode which limits the current carrying capacity of the electrode. As shown in the current-voltage curves of the Virkar et al. patent, the experimental current is limited to 0.5 A/cm$^2$ for the Pt/YSZ and LSM/YSZ cathodes disclosed therein.

Therefore, there is a need in the art for a composite electrode which mitigates the limitations of the prior art, allowing higher performance solid state ionic devices and solid oxide fuel cells in particular.

SUMMARY OF THE INVENTION

The present invention is directed at an electrode having an improved microstructure which achieves a high density of active electrochemical reaction sites between the electrolyte and electrode and incorporates electrocatalytic materials such as noble metals into the electrode in an intimate fashion. As well, the improved microstructure may have better long-term structural stability of the cell by reducing the effects of noble metal catalyst sintering and vapor loss. The electrode may be incorporated into any solid state electrochemical devices such as oxygen pumps, membranes and sensors, solid state batteries or solid oxide fuel cells. The electrode of the present invention may be either a cathode or an anode.

Accordingly, in one aspect of the invention, the invention comprises an electrode forming part of a solid state electrochemical device, said electrode bonded to a dense electrolyte layer and comprising a porous three-dimensional solid phase comprising:
  (a) an electrocatalytic phase comprising a plurality of electrocatalytic particles;
  (b) an ionic conducting phase comprising a plurality of ionic conductor particles;
  wherein said electrocatalytic conducting phase and ionic conducting phase are interspersed and wherein the mean size of said electrocatalytic particles is substantially equal to or larger than the mean size of said ionic conducting particles.

The electrode of the present invention is formed by mixing ceramic ion conductor particles and noble metal electrocatalyst particles into a composite electrode which is then applied to a dense electrolyte substrate by screen printing or by similar well-known methods. The resulting electrode microstructure is highly porous and includes very long three-phase boundaries, direct ion conducting channels from the catalytic sites to the electrolyte and direct electron conducting channels through the electrode to the catalytic sites. The electrocatalyst particles are preferably comprised of a noble metal and are preferably larger than the ion conductor particles which results in a morphology where the ion conductor particles pin the boundaries of the noble metal particles. The relatively large noble metal particle size reduces vapor loss at elevated temperatures while grain boundary pinning reduces or prevents sintering or coalescing of the noble metal particles.

In one embodiment, the ion conductor particles may comprise ceramic particles which may preferably be yttrium stabilized zirconia and the noble metal particles may comprise palladium. Those skilled in the art will be aware of other materials which will function as ion conducting particles or as electrocatalytic particles.

In one embodiment, the invention may comprise an electrode comprising (a) an electrode functional layer for use in a solid state electrochemical device, said layer comprising a porous three dimensional structure comprising linked particles of an electrocatalytic material and linked particles of an ionic conductor wherein the median size of the electrocatalyst particles is approximately equal to or larger than the median size of the ion conducting particles; and (b) a long range conducting electrode layer that is applied on top of the functional layer. In a planar SOFC, long range conductivity refers to horizontal conductivity between the ribs of an interconnect plate, rather than the short range vertical conducting path through the functional layer. The conducting layer may comprise electronically conductive metal oxides such as lanthanum cobaltate.

In another aspect, the invention comprises a solid state electrochemical device comprising a porous anode, a dense electrolyte and a cathode comprising a porous three-dimensional structure comprising linked particles of an electrocatalytic material and linked particles of an ionic conductor wherein the mean or median size of the electrocatalyst particles is larger than the mean or median size of the ion conducting particles. The solid state electrochemical device may be a solid oxide fuel cell.

In another aspect of the invention, the invention is a method of forming an electrode for use in a solid state electrochemical device having a dense electrolyte layer comprising the steps of:
  (a) mixing electrocatalytic particles with ion conducting particles where mean or median size of the electrocatalytic particles is substantially equal to or larger than the mean or median size of the ion conducting particles; and (b) creating a porous three-dimensional structure bonded to the dense electrolyte layer, said structure comprising linked particles of the noble metal particles and linked particles of the ionic conductor.

In one embodiment, a further conducting layer of a metal oxide may be applied but not presintered to the electrode. The metal oxide may comprise lanthanum cobalt oxide.

BRIEF DESCRIPTION OF THE DRAWINGS

The invention will now be described by way of exemplary embodiments with reference to the accompanying drawings. In the drawings.

DETAILED DESCRIPTION OF THE INVENTION

The present invention provides for a composite electrode for use with a solid oxide fuel cell and further provides for a method of making such an electrode. When describing the present invention, all terms not specifically defined herein have their common art-recognized meanings.

A. Definitions

As used herein, the term "about" refers to a range of values that is the stated value plus or minus 10%.

As used herein, the term "electrocatalyst" refers to a material which is both electronically conducting and a catalyst for an electrode reaction. Electrocatalyst materials may include noble metals and certain metal oxides.

As used herein, the term "noble metal" refers to metals and alloys of the group comprising silver, gold, iridium, osmium, palladium, ruthenium, rhodium and platinum.

As used herein, the term "LC" or "lanthanum cobaltate" refers to $LaCoO_3$.

B. Description

Figure 1:
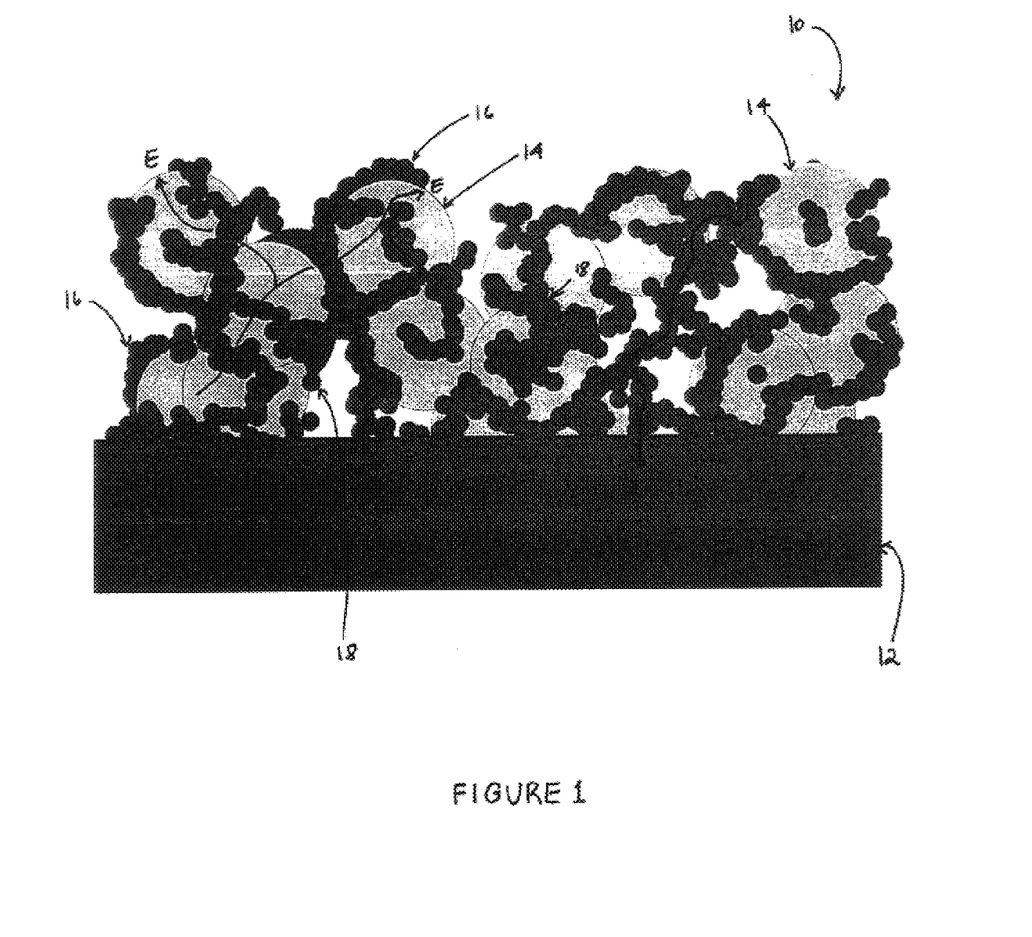
FIG. 1 is a schematic representation of a cross-sectional view of a cathode according to one embodiment of the present invention.

As shown in FIG. 1, one embodiment of a porous composite electrode (10) is shown bonded to an electrolyte (12). The composite electrode is formed from electrocatalytic noble metal particles (14), and from ion conducting ceramic particles (16) which are bonded intimately to the electrolyte (12). The ceramic particles combine to form ionic conducting paths (I) from the electrolyte (12) to the electrochemical active sites (18). The metal phase forms electronic conducting paths (E) through the electrode (10) to the contact paste (not shown) and cathode electronical conducting strip (not shown). The electrochemical active area coincides with the three phase boundary (18) which extends along the common boundary of the gaseous pore phase, the ceramic phase (16) and the noble metal phase (14). It is generally believed that the electrode reaction substantially takes place at this boundary, where the three phases (gas, electrocatalyst conductor and ion conductor) meet.

Thus, the composite electrode of the present invention may provide more electrode reaction sites to lower the overpotential loss. Furthermore, the presence of catalytic noble metals at the electrochemical active areas (18) lowers the activation energy for the electrode reactions.

The ceramic ionic conducting phase in the composite electrode may be any known ion conductor such as yttria stabilized zirconia (YSZ). In a preferred embodiment, the ceramic phase is preferably the same material as the electrolyte so that interface between the ceramic phase and the electrolyte is chemically stable and there is a good thermal match between the two materials.

The electrocatalytic phase may be any noble metal or noble metal alloy. These metals all have catalytic effect for the reduction of oxygen and are good electronic conductors. In a preferred embodiment, palladium is used because its coefficient of thermal expansion is similar to that of the YSZ which may be used as the electrolyte and in the ceramic phase. Accordingly, the use of palladium and YSZ in the preferred composite electrode of the present invention provide good thermal stability even where the electrode is subjected to thermal cycling.

The relative proportion of the noble metal and ceramic ionic conducting phases may be varied. However, if the volume percentage of one phase is lowered too far, continuous channels of that phase may not form when the electrode is formed. It is preferable to have continuous ionic conducting channels, electronic conducting channels and porous channels throughout the composite electrode thickness.

The electronic conducting channels lowers the ohmic resistance of the cell. Electronic conductivity of the composite electrode may be increased by increasing the particle size of the noble metals and by increasing the volume percentage of the metal phase. However, increasing the particle size decreases the catalytic effect of the electrocatalyst. Ionic conductivity may be increased by decreasing the particle size of the ceramic material and by increasing the volume percentage of the ceramic phase. However, a longer three phase boundary is created by using smaller particles of either the ceramic or metal phase.

As shown in the Figures, because the ceramic particles are preferably smaller than the metal particles, the ceramic particles (16) partially cover the noble metal particles (14). This reduction in surface area of the metal phase reduces vapor loss of the noble metal at elevated operating temperature. Moreover, the ceramic particles (16) tend to agglomerate between two adjoining metal particles (14), in an effect known as grain boundary pinning, which prevents further sintering of noble metal particles. Thus, the morphology of the electrode, the electrode/electrolyte interface and the three phase boundary may be more stable.

Figure 2:
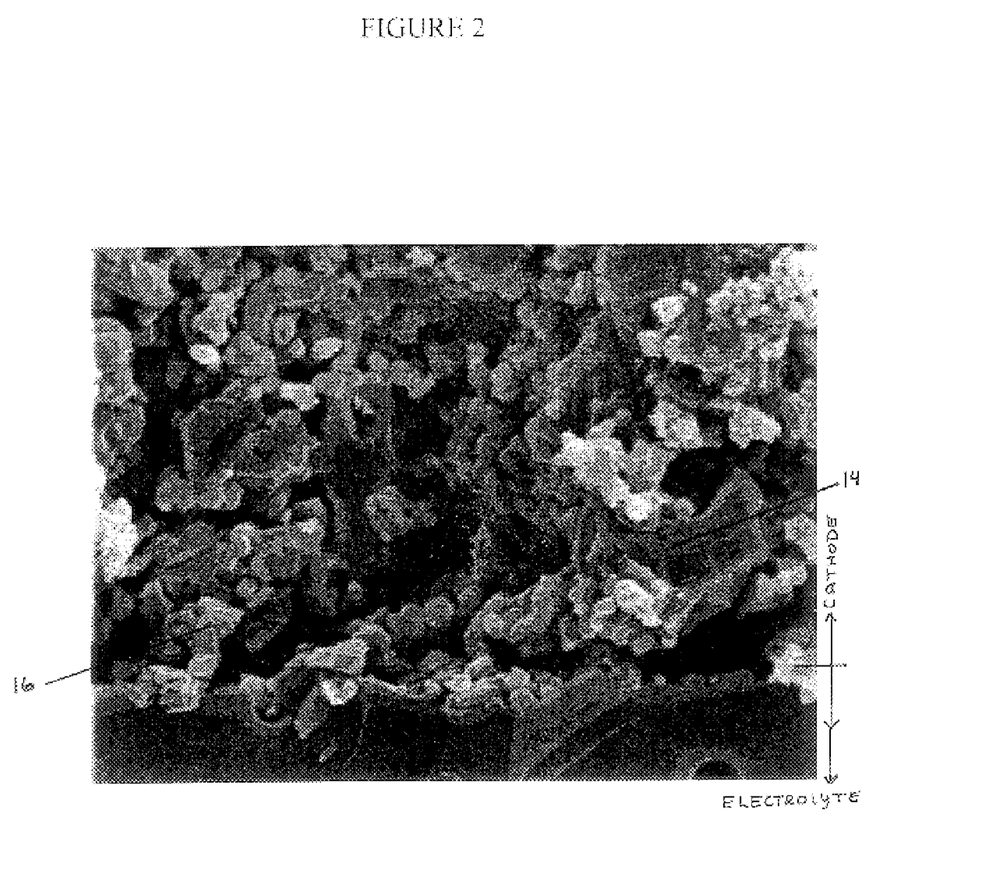
FIG. 2 is a scanning electron micrograph of a cathode cross-section according to one embodiment of the present invention.

In one embodiment illustrated in FIG. 1, the gas phase, the metal phase and the ceramic phase are approximately equal in volume percent. However, the metal particles are approximately 5 to 10 times the size of the ceramic particles. The resulting microstructure is as shown in FIG. 1 and FIG. 2. As is apparent, the ceramic particles form continuous ion conducting channels in the form of particle chains to the electrolyte from the three phase boundary. The metal particles connect to form continuous electron conducting channels between the three phase boundary and the cathode conducting layer. Finally, the high porosity of the structure combined with the intertwining of the ion conducting channels and the electron conducting channels creates a tremendously large three phase boundary.

A feature of the present invention is the relative size of the metal particles compared to the ceramic particles. The metal particles should preferably be larger than the ceramic particles and more preferably about 2 to 10 times larger. As a result of this size differential, the ceramic particles tend to agglomerate on the metal particles in continuous strings. In particular, the ceramic particles agglomerate along the contact patches of adjoining metal particles. As referred to above, this morphology not only increases the three phase boundary of the cathode but also reduces sintering of the metal particles and reduces evaporative loss of the metal.

An electrode according to the present invention may be applied to an electrolyte/anode substrate according to well known suitable techniques such as screen printing, tape casting, slip casting, vapor deposition or thermal spraying. A preferred method is screen printing using a paste formed from a suitable binder, a suitable solvent, the noble metal particles and the ion conductor particles. The nature and use of the binder and the solvent are well known to those skilled in the art.

Figure 4:
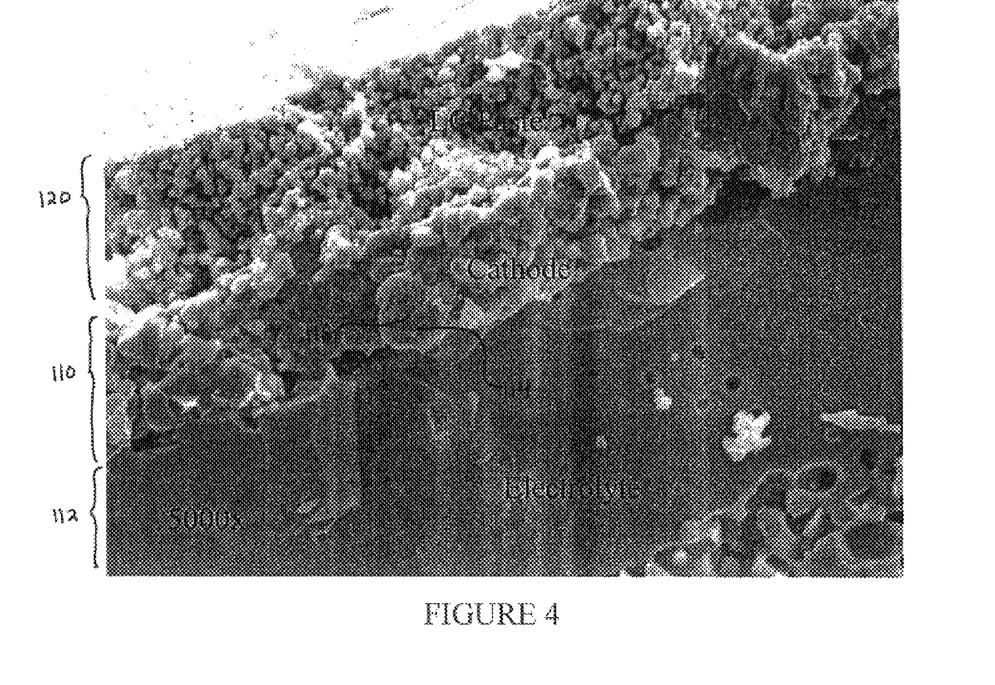
FIG. 4 is a scanning electron micrograph (5000×) of a cathode cross-section of another embodiment of the invention.
Figure 5:
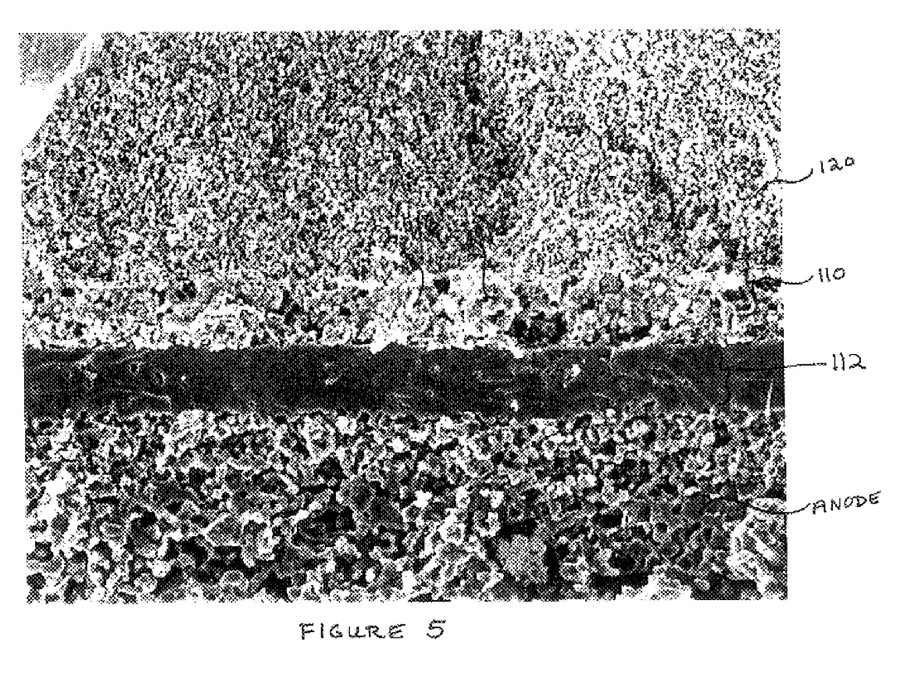
FIG. 5 is a scanning electron micrograph of an alternative embodiment of a cathode in cross-section.

In an alternative embodiment of the invention, a porous composite functional cathode layer (110) is shown bonded to an electrolyte (112) in FIGS. 4 and 5. The composite functional layer (110) is formed from electron conducting and catalytic noble metal particles (114), and from ion conducting ceramic particles (116) which are bonded intimately to the electrolyte (112). Covering the functional layer (110) containing the catalytic noble metal particles (114) and the ion conducting ceramic particles (116) is a high electronically conductive layer (120). In one embodiment, the electronically conductive layer (120) is made from LC material. Other suitable materials for use in an oxidizing environment may include LSM ($LaSrMnO_3$), or other electronically conducting metal oxides.

In one embodiment the functional layer (110) comprises noble metal particles about 1 $\mu$m in diameter and is about 1–5 $\mu$m thick, and thus is about 1 to 5 particles thick. This provides a layer with good short range vertical electronical conductivity, since the probability of noble metal particles providing an electronical conducting path between the electrolyte and the LC layer (120) is greatly increased over the prior art, which features thicker layers and the same quantities of noble metals. The ceramic particles are preferably smaller than the metal particles and may be in the range of about 0.1 to 0.2 $\mu$m in diameter.

Figure 9:
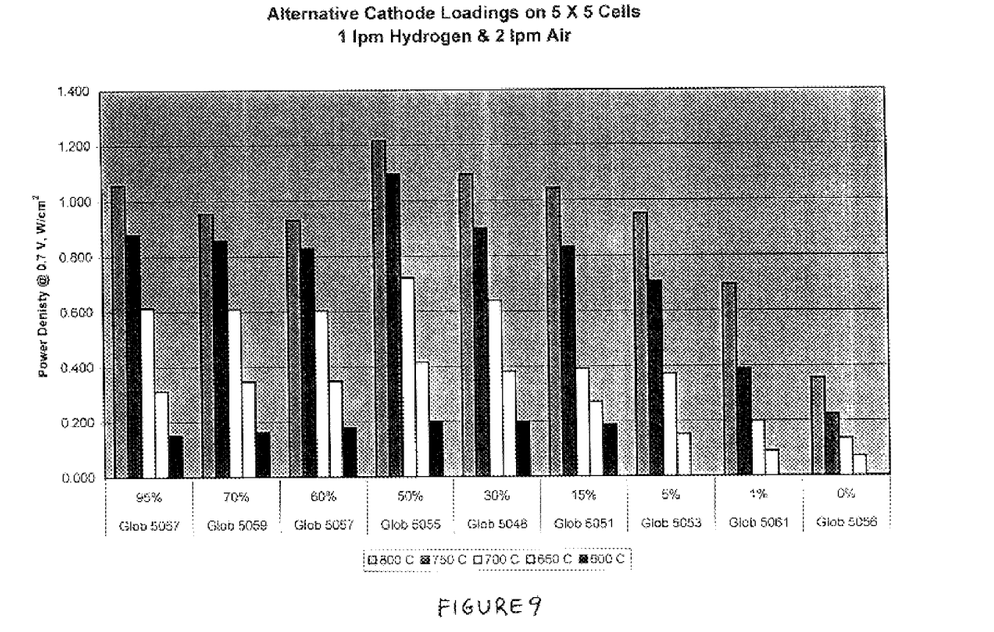
FIG. 9 shows the effects of altering the noble metal concentration on power density, with tests conducted at different temperatures.

In one embodiment, the electrode layer (10) or the noble metal functional layer (110) is comprised of 50% electrocatalytic particles and 50% ion conducting particles with about 33% porosity by volume. In other words, the electrode comprises ⅓ ion conducting particles, ⅓ electrocatalytic particles, and ⅓ pore space by volume. All references herein to volume percentage of the electrocatalytic phase is of the volume of the solid phase. This volume percentage of the electrocatalyst may be varied between about 1.0% and about 95% by volume of the solid portion of the electrode, and preferably between about 20% to about 60%, depending upon the cost target to be achieved, desired performance per cell, or other factors. The volume percentage of the electrode taken by pore space is preferably about 30% or ⅓, although the electrode porosity may be higher or lower.

Where the electrocatalyst is a noble metal, the volume percentage of noble metal may be between about 1% to about 50% to achieve a good balance between cost and performance. As shown in FIG. 9, there is no increase in performance in cells having a noble metal content in the functional layer (110) higher than 50%, therefore the additional cost of the extra noble metal is not preferred. Where the highest performance is desired, the noble metal content is preferably about 50%. Where a balance of performance and cost is desired, the noble metal content is preferably about 5%. Although the cell performance decreases as the noble metal content is decreased towards 1%, the loss in performance may be offset by the reduced cost of manufacturing the cell.

Figure 6:
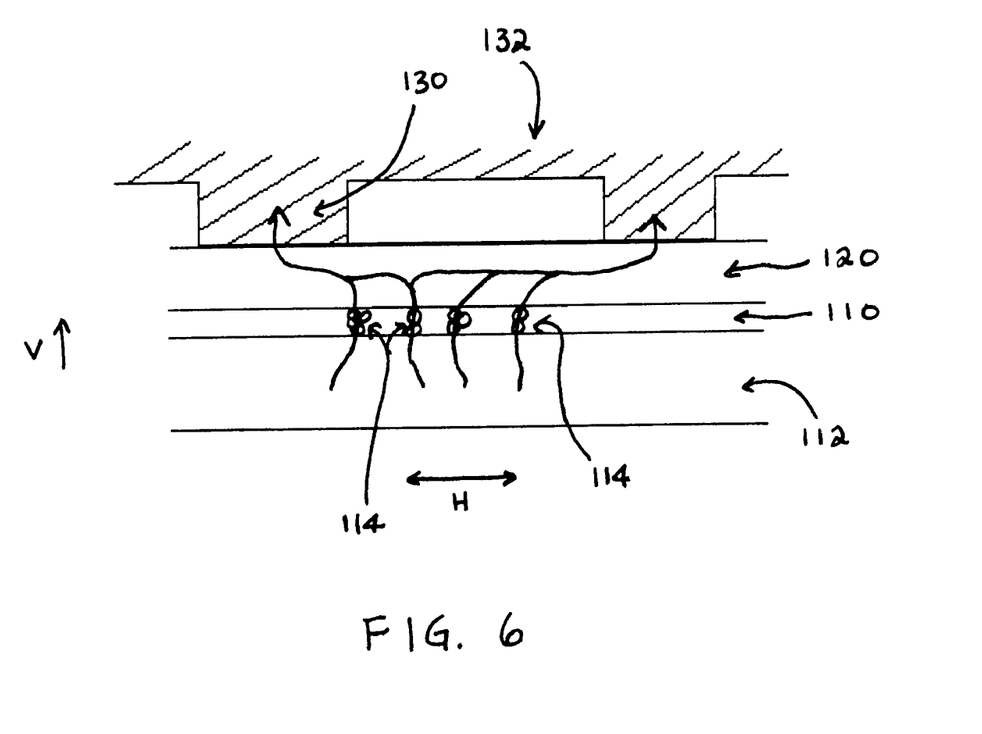
FIG. 6 is a schematic depiction of current flow through the cathode and the conducting electrode.

In an embodiment where the noble metal layer is thin, less than about 5 $\mu$m, and when the concentration of noble metals is below about 30 vol %, vertical conductivity (as indicated by arrow V in FIG. 6) is much more probable than horizontal long range conductivity (H) because of the distribution of the noble metal particles. There may not enough metal particles to provide continuous long range (H) conducting paths to carry current to the relatively widely spaced ribs (130) of the interconnect plate (132). To overcome this difficulty, an electrode (120) of electronically conducting material is applied over the functional layer (110). This conducting electrode (120) may preferably be in the order of about 15 to about 20 $\mu$m in thickness, but can vary from about 3 to about 100 $\mu$m. The conducting electrode or "LC layer" (120) material is preferably lanthanum cobaltate ($LaCoO_3$) which, in an oxidizing environment, has very good electronic conductivity properties although other suitable conductive materials may be used.

The LC layer is preferably not prefired prior to operation in the stack because it is preferred to avoid sintering of the LC layer. Once sintered, the LC layer has a thermal expansion rate about twice that of the remaining components in the fuel cell, with the resultant sealing and bonding problems due to thermal expansion mismatch. Also, LC can chemically react with YSZ forming undesirable phases at the high temperature encountered during sintering. For this reason, the LC layer is preferably not sintered prior to use within the fuel cell stack.

The combination of the thinner noble metal functional layer (110) and the long range electronic conducting LC layer (120) have produced a fuel cell that delivers improved performance over the prior art, and may deliver power densities in the region of 1.2 W/cm$^2$ as shown in FIG. 9.

The following examples are intended to be illustrative of the claimed invention but not limiting thereof.

EXAMPLE 1

This example discloses a method of making a Pd and YSZ composite cathode for an anode supported solid oxide fuel cell. The resulting cathode is schematically illustrated in FIG. 1. A scanning electron micrograph of a cathode made in accordance with this example is shown in FIG. 2.

A screen printable composite cathode paste was made up of equal volumes of well-dispersed Pd particles, 8 mole percent yttria stabilized zirconia (8YSZ) in alpha-terpineol. Ethyl-cellulose binder was added in an effective amount. The Pd particle size ranged from 0.5 to 2 $\mu$m with a median size of about 1 $\mu$m while the 8YSZ particle size ranged from 0.1 to 0.2 $\mu$m with a median size of about 0.17 $\mu$m. The substrate (100 mm in square) consisted of a fully dense 8YSZ electrolyte (10 $\mu$m thick) on a porous NiO-8YSZ anode (1 mm thick). The cathode paste was screen printed on the electrolyte side of the substrate. The foot prints were 90 mm in square. The prints were oven dried at 60–80° C., then fired at 1300° C. in air for 2 hours. The thickness of the composite cathode after firing was about 5–10 µm. The resulting solid phase was 50% vol Pd and 50% vol YSZ with approximately 33% porosity.

A comparison of the resulting Pd/8YSZ cathode cell with a similar cell with a common perovskite cathode (LSM) showed that the cell with Pd/8YSZ cathode had much better performance. A 15-cell stack made from cells with this composite cathode was tested at 750° C. and achieved a power of 750 W with hydrogen/argon (50/50) mixture as the fuel. Current interrupt experiments showed that the improvement resulted from both lower ohmic resistance at the cathode due to the palladium conductivity network and lower overpotential loss due to an increase in the electrochemical active area (three-phase boundary) and catalytic active area (palladium surface).

Figure 3:
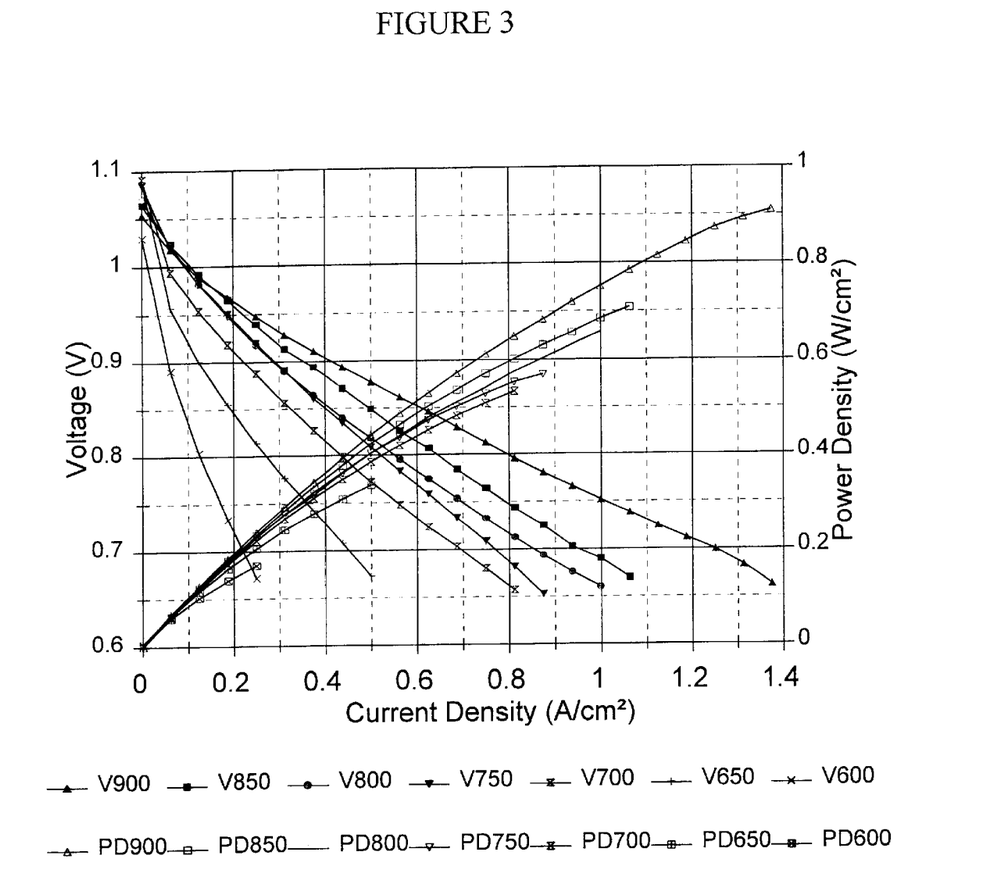
FIG. 3 is a graph of the I–V characteristics of a single fuel cell of the present invention.

FIG. 3 illustrates the I–V characteristics of a single fuel cell incorporating this embodiment of an electrode operating at temperatures varying from 600° C. to 900° C.

EXAMPLE 2

This example discloses a Pd, YSZ, and LC composite cathode for an anode supported solid oxide fuel cell and a method of making such a cathode. A scanning electron micrograph of the resulting cathode is illustrated in FIG. 4.

A screen printable composite cathode functional layer paste was made up of suitable volumes of well dispersed Pd particles and 8YSZ in alpha terpineol to achieve a solid phase of 5% Pd/95% 8YSZ. Ethyl cellulose binder was added in an effective amount. The Pd particle size ranged from 0.5 to 2 µm with a median size of about 1 µm while the 8YSZ particle size ranged from 0.1 µm to 0.2 µm with a median size of about 0.17 µm. The substrate (100 mm square) consisted of a fully dense 8YSZ electrolyte (10 µm thick) on a porous NiO—8YSZ anode (1 mm thick). The cathode functional layer paste was screen printed on the electrolyte side of the substrate. The footprints were 90 mm square. The prints were oven dried at 60–80° C., then fired at 1300° C. in air for 1 hour. The thickness of the composite functional layer after firing was about 1–3 µm. The LC layer was screen printed to a thickness of about 3 µm on top of the functional layer but was not sintered. Once the cell is at operating temperature of 800° C. the LC powder bonded adequately to the functional layer.

Figure 7:
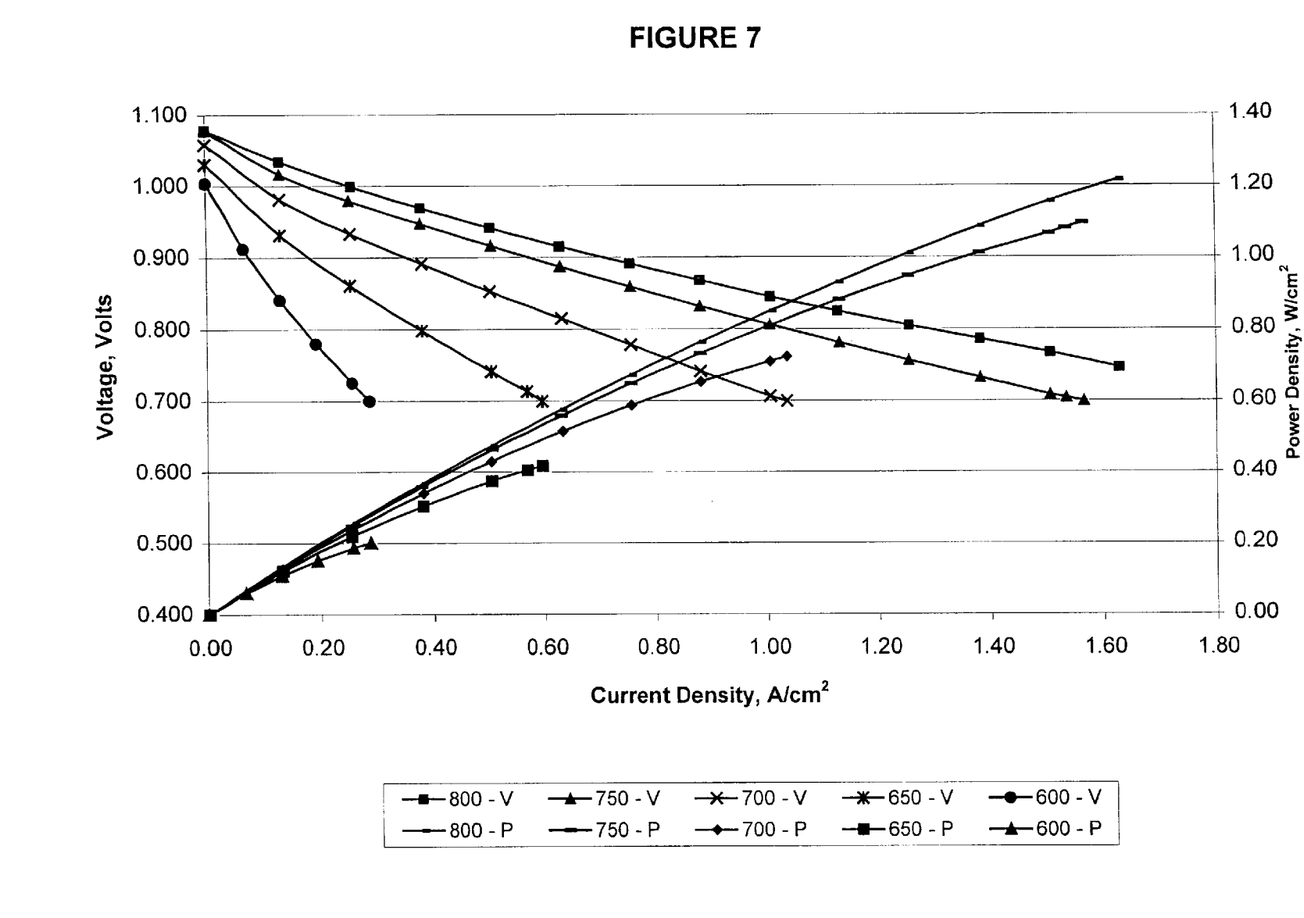
FIG. 7 is a graph of the I–V characteristics of one alternative embodiment of a single fuel cell.

FIG. 7 illustrates the I–V characteristic of a single fuel cell incorporating this embodiment of a cathode at operating temperatures varying from 600° C. to 900° C.

Figure 8:
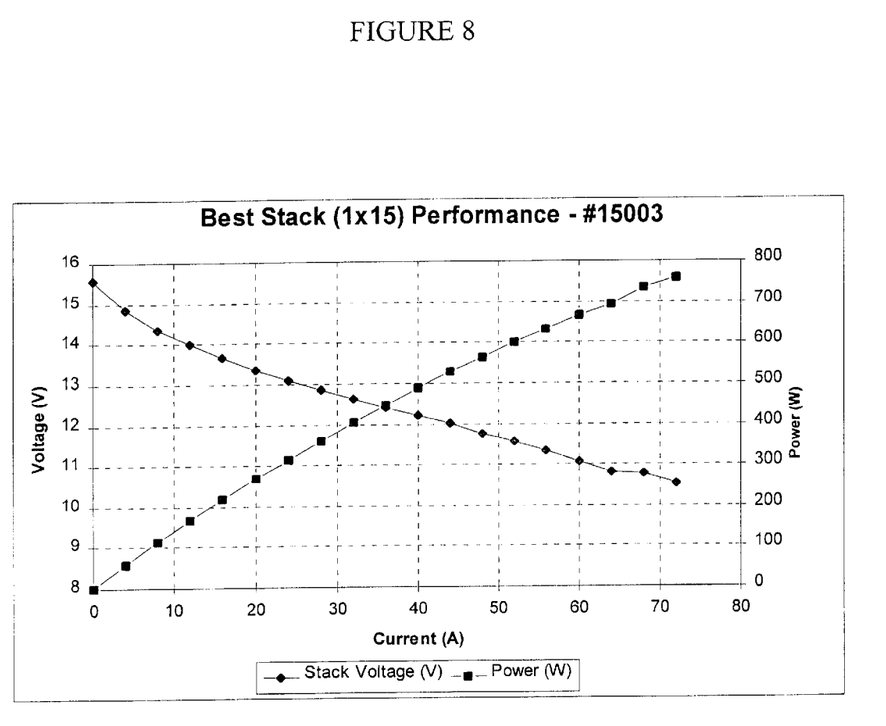
FIG. 8 is a graph of the I–V characteristic of one embodiment of a 15 fuel cell stack.

FIG. 8 illustrates the I–V performance of a stack of 15 fuel cells incorporating this embodiment of a cathode.

EXAMPLE 3

A composite cathode was screen printed in a similar manner as Example 2 above but to a thickness of about 10 µm. The LC layer was again screen printed on top of the functional layer but to a thickness exceeding 30 µm. A scanning electron micrograph showing the resulting cathode in cross-section is shown in FIG. 5.

EXAMPLE 4

FIG. 9 illustrates the effect on power density (w/cm$^2$ at 0.7 v) of varying the proportion of palladium from 0% vol to 95% vol of the solid phase. As may be seen, performance is maximized with 50% vol Pd. However, significant performance is still achieved with Pd loading as low as 5% vol.

As will be apparent to those skilled in the art, various modifications, adaptations and variations of the foregoing specific disclosure can be made without departing from the scope of the invention claimed herein.

What is claimed is:

1. A cathode forming part of a solid oxide fuel cell comprising a dense electrolyte layer and an anode layer, said cathode comprising a porous three-dimensional solid phase comprising:

(a) an electrocatalytic phase comprising a plurality of electrocatalytic particles;

(b) an ionic conducting phase comprising a plurality of ionic conductor particles;

wherein the electrocatalytic phase and the ionic conducting phase are interspersed, the mean size of the electrocatalytic particles is substantially equal to or larger than the mean size of the ionic conducting particles, and wherein the cathode is less than about 10 µm thick.

2. The cathode of claim 1 wherein the cathode is less than about 5 µm thick.

3. The cathode of claim 2 wherein the cathode is less than about 3 µm thick.

4. An electrode forming part of a solid state electrochemical device, said electrode bonded to a dense electrolyte layer and comprising a porous three-dimensional solid phase comprising:

(a) an electrocatalytic phase comprising a plurality of electrocatalytic particles;

(b) an ionic conducting phase comprising a plurality of ionic conductor particles;

wherein the electrocatalytic phase and the ionic conducting phase are interspersed, the mean size of the electrocatalytic particles is substantially equal to or larger than the mean size of the ionic conducting particles, and wherein the electrode has a vertical dimension and a horizontal dimension and said electrocatalytic phase provides continuous electronic conductivity in the vertical dimension but not in the horizontal dimension.

5. An electrode forming part of a solid state electrochemical device, said electrode bonded to a dense electrolyte layer and comprising a porous three-dimensional solid phase comprising:

(a) an electrocatalytic phase comprising a plurality of electrocatalytic particles;

(b) an ionic conducting phase comprising a plurality of ionic conductor particles;

wherein the electrocatalytic phase and the ionic conducting phase are interspersed, the mean size of the electrocatalytic particles is substantially equal to or larger than the mean size of the ionic conducting particles, and wherein said electrode further comprises a horizontally electronic conducting layer comprising an electronically conductive metal oxide.

6. The electrode of claim 5 wherein said electronically conductive metal oxide comprises lanthanum cobaltate.

7. An electrode forming part of a solid state electrochemical device, said electrode bonded to a dense electrolyte layer and comprising a porous three-dimensional solid phase comprising:

(a) an electrocatalytic phase comprising a plurality of electrocatalytic particles;

(b) an ionic conducting phase comprising a plurality of ionic conductor particles;

wherein the electrocatalytic phase and the ionic conducting phase are interspersed, the mean size of the electrocatalytic particles is substantially equal to or larger than the mean size of the ionic conducting particles, and wherein the ionic conductor particles are comprises of YSZ.

8. A solid oxide fuel cell comprising a porous anode, a dense electrolyte and a cathode comprising a porous three-dimensional structure comprising linked particles of palladium and linked particles of an ionic conductor wherein the mean or median size of the palladium particles is larger than the mean or median size of the ionic conductor particles.

9. The fuel cell of claim 8 wherein the mean or median palladium particle size is at least about 2 times larger than the mean or median ion conductor particle size.

10. The fuel cell of claim 9 wherein the mean or median electrocatalytic particle size is about 4 to about 10 times larger than the mean or median ion conductor particle size.

11. The fuel cell of claim 8 wherein the ionic conductor is comprised of the same ion conducting material as the electrolyte layer.

12. The fuel cell of claim 11 wherein the electrolyte and ion conducting particles are both comprised of YSZ.

13. The fuel cell of claim 8 wherein the cathode is less than about 10 μm thick.

14. The fuel cell of claim 13 wherein the cathode is less than about 5 μm thick.

15. The fuel cell of claim 14 wherein the cathode is less than about 3 μm thick.

16. A solid oxide fuel cell comprising a porous anode, a dense electrolyte and a cathode comprising a porous three-dimensional structure comprising linked particles of an electrocatalytic material and linked particles of an ionic conductor wherein the mean or median size of the electrocatalytic particles is larger than the mean or median size of the ionic conductor particles, and a long range electronically conductive layer applied to the cathode.

17. The fuel cell of claim 16 wherein said long range electronically conductive layer is comprised of lanthanum cobaltate.

18. The fuel cell of claim 17 wherein said long range electronically conductive layer is not sintered prior to operation of the fuel cell.

19. The fuel cell of claim 7 or 16 wherein the electrocatalytic material is a noble metal.

20. The fuel cell of claim 19 wherein the noble metal is palladium.

21. The fuel cell of claim 7 or 16 wherein the cathode is less than about 10 μm thick.

22. An electrode forming part of a solid oxide fuel cell comprising a dense electrolyte layer, said electrode comprising a porous three-dimensional solid phase comprising:
 (a) an electrocatalytic phase comprising a plurality of electrocatalytic particles;
 (b) an ionic conducting phase comprising a plurality of ionic conductor particles;
 wherein the electrocatalytic phase and the ionic conducting phase are interspersed, the mean or median size of the electrocatalytic particles is substantially equal to or larger than the mean or median size of the ionic conducting particles, and wherein the solid phase of the electrode comprises 65% or less electrocatalytic particles by volume.

23. The electrode of claim 22 wherein the electrode is a cathode.

24. The cathode of claim 23 wherein the cathode is less than about 10 μm thick.

25. The cathode of claim 23 wherein the electrocatalytic particles are comprised of a noble metal.

26. The cathode of claim 25 wherein the noble metal is comprised of palladium.

27. The cathode of claim 23 wherein the ionic conducting particles are comprised of YSZ.

28. A solid oxide fuel cell comprising an electrode as claimed in claim 22.

29. The solid oxide fuel cell of claim 28 wherein the electrode is a cathode.

* * * * *